United States Patent [19]  [11] 4,454,831
Gallo  [45] Jun. 19, 1984

[54] WATERING INDICATOR FOR HANGING PLANTS

[76] Inventor: Joseph S. Gallo, 58 Peach St., Walpole, Mass. 02081

[21] Appl. No.: 513,736

[22] Filed: Jul. 14, 1983

[51] Int. Cl.³ .................. G01N 5/02; G01L 11/24; A01G 9/02; G01G 23/20
[52] U.S. Cl. .................................... 116/200; 116/212; 116/215; 73/73; 47/67; 177/45; 177/50; 177/233
[58] Field of Search ............. 116/109, 34 R, 215, 116/297, DIG. 32; 73/73, 296, 862.53, 337; 47/67, 39; 177/45, 50, 225, 229, 233, 234, 232

[56] References Cited

U.S. PATENT DOCUMENTS

| | | | |
|---|---|---|---|
| 479,718 | 7/1892 | Morgan et al. | 177/232 |
| 3,117,442 | 1/1964 | Brooks | 116/200 |
| 3,260,233 | 7/1966 | Bergunder | 116/34 R |
| 3,967,578 | 7/1976 | Gallo | 116/297 |
| 4,078,625 | 3/1978 | Loeb | 47/39 |
| 4,238,002 | 12/1980 | Hexamer | 47/67 |

Primary Examiner—Charles Frankfort
Assistant Examiner—W. Morris Worth

[57] ABSTRACT

A watering indicator for hanging plants, with two support elements (e.g., an upper hook attached to a tubular housing and a lower hook integral with a rod extending into the housing), a spring resisting separation of the support elements (e.g., located within the housing and surrounding the rod), a mask element connected to one support element and adapted to be moved along that element when the two elements move relative to one another, an indicator element with an indication indicia (e.g., a brightly-colored band) mounted to the other support element, all adapted so that the indication indicia is covered by the mask element when the plant is watered and is later exposed when the plant dries out.

11 Claims, 4 Drawing Figures

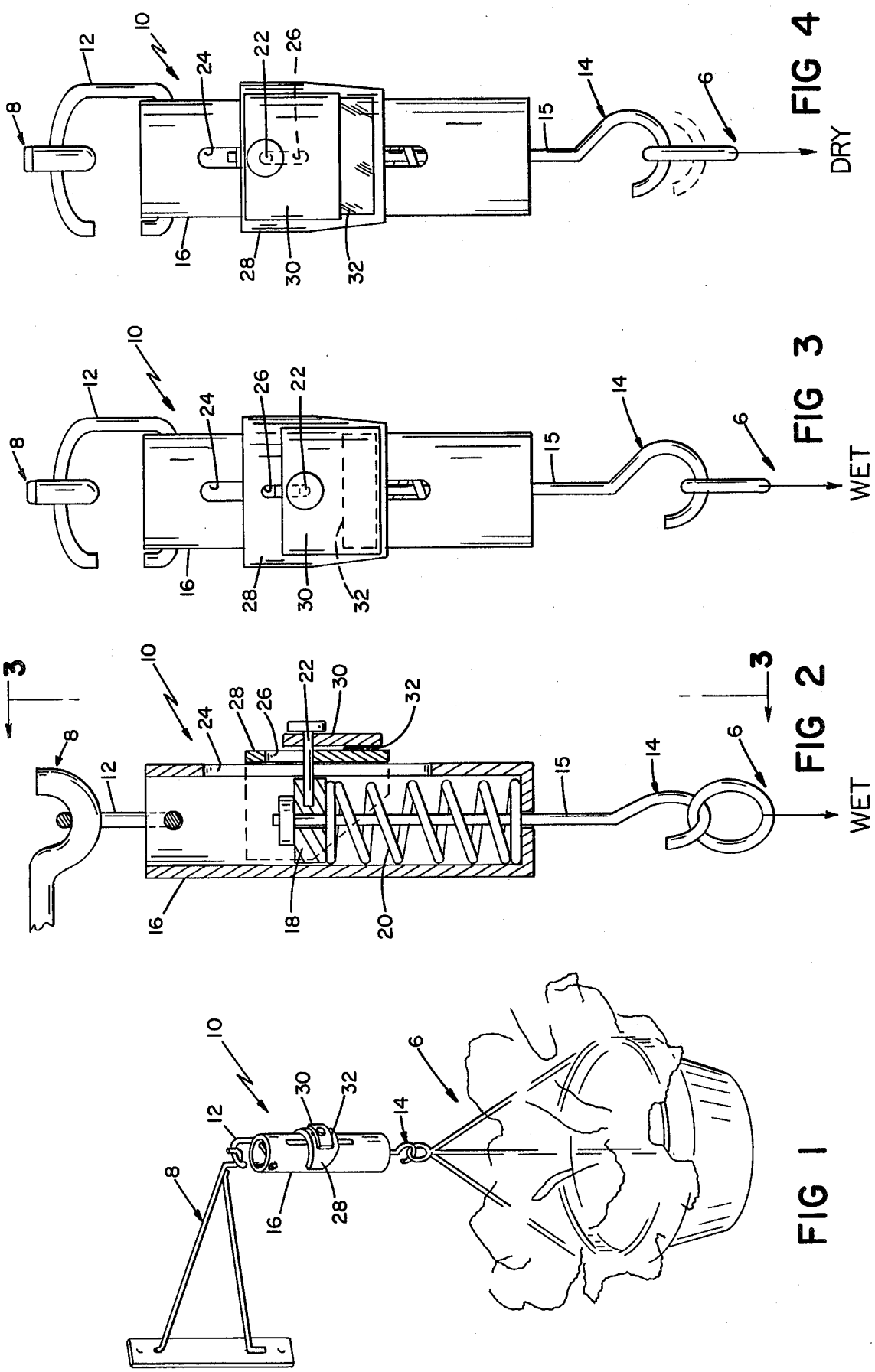

WATERING INDICATOR FOR HANGING PLANTS

BACKGROUND OF THE INVENTION

This invention relates to a watering indicator for hanging plants. It would be desirable to provide a means of indicating when a plant needs watering. This is particularly true for hanging plants, which are often hung so that is is not easy to inspect the soil for moisture content. Moreover, the frequency with which plants require watering varies with the type of plant and with the climatic conditions in the plant's vicinity.

I designed and sold prior to this invention a watering indicator known as the Reliable Plant Guide. When a plant was watered, a rubber washer was moved downward on an indicator shaft by downward deflection of a pointer arm extending from a torsion spring. When the plant dried out, the pointer arm moved upward away from the rubber washer. The indication of need for water was the separation of the pointer from the rubber washer. To accommodate different weight plants, the user had to hook the plant to the indicator at differing positions along the pointer arm.

SUMMARY OF THE INVENTION

I have discovered an improved watering indicator for hanging plants. The indicator is extremely simple to use, it provides an improved visual indication of the need for watering, and it can easily accommodate a wide range of plant weights.

In general the invention features two support elements (e.g., an upper hook attached to a tubular housing and a lower hook integral with a rod extending into the housing), a spring resisting separation of the support elements (e.g., located within the housing and surrounding the rod), a mask element connected to one support element and adapted to be moved along that element when the two elements move relative to one another, an indicator element with an indication indicia (e.g., a brightly-colored band) mounted to the other support element, all adapted so that the indication indicia is covered by the mask element when the plant is watered and is later exposed when the plant dries out.

In preferred embodiments, the indicator element is frictionally mounted on one support element so that, when the direction of relative motion between the two support elements changes (i.e., when the plant is watered or begins to dry out), the indicator element remains fixed in place while the mask element moves a distance sufficient to cover (when the plant is watered) or expose (when the plant dries out) the brightly-colored indication band; a slot is provided in the indicator element to allow it to remain fixed in place as described; the mask element is connected to its associated support element by a member passing through the slot in the indicator element; and the spring is a helical (e.g., compression) spring.

Other advantages and features of the invention will be apparent from the following description of a preferred embodiment and from the claims.

DESCRIPTION OF THE PREFERRED EMBODIMENT

The structure and use of a preferred embodiment of my invention will now be described, after first briefly describing the drawings.

FIG. 1 is an elevation view of said preferred embodiment installed between a hanging plant and its support.

FIG. 2 is a cross-sectional view illustrating the parts of the assembled watering indicator.

FIG. 3 is an elevation view, showing the indicator in the wet position (no watering required).

FIG. 4 is an elevation view, showing the indicator in the dry position (watering required).

Illustrated in the drawings is a watering indicator 10 installed between hanging plant 6 and support 8. Hooks 12, 14 on the indicator are used to make the attachments between the support and plant. Upper hook 12 is attached to the top of cylindrical housing 16. Lower hook 14 is an integral extension of rod 15, which extends through the interior of the housing to plate 18, and which can rotate relative to housing 16 and upper hook 12, to allow plant 6 to be easily rotated. Helical spring 20 is compressed between plate 18 and the base of the housing. A pin 22 extends from plate 18 through longitudinal slot 24 in the housing and through slot 26 in an indicating element 28 to connect the plate to a masking element 30. The indicating element 28, which is positioned between masking element 30 and the housing, has a brightly-colored band 32 that is exposed when the hanging plant needs watering. The indicating element grips the housing tightly enough to maintain it in whatever position it is moved. This frictional grip of the indicating element on the housing is preferably achieved by forming it from a cylindrical section of the same diameter as the housing.

When in use, upper hook 12 will be attached to support 8 and hook 14 to plant 6. When the plant is watered, the increased weight of the plant compresses spring 20 and thereby lowers masking element 30 over brightly-colored band 32, as shown in FIG. 3. After masking element 30 has covered band 32, pin 22 will be at the bottom of slot 26, and further compression of spring 20 will pull masking element 30 and indicating element 28 down housing 16 in unison, how far depending on the weight of the plant and the amount of water applied.

As the plant dries out, the reduction in weight causes a gradual extension of spring 20 (and an upward movement of lower hook 14, as illustrated in FIG. 4). This causes masking element 30 to uncover brightly-colored band 32 as shown in FIG. 4. This occurs because indicating element 28 remains fixed in the position it assumed when the plant was first watered and does not move upwardly until pin 22 reaches the top of slot 26, which happens after brightly-colored band 32 is exposed. The band will remain exposed until the plant is again watered. Even if the masking element continues to rise after pin 22 reaches the top of slot 26, the masking element 30 and indicator element 28 will simply move upwardly in unison with band 32 remaining exposed.

Other embodiments of the invention are within the following claims. For example, a tension spring could replace compression spring 20.

What is claimed is:

1. Apparatus for supporting a hanging potted plant and for indicating when the plant needs watering, said aparatus comprising:
    first and second support elements for connecting said plant to an overhead support, one said element being connected to said overhead support and the other said element being connected to said potted plant, spring means connecting said support elements for supporting the weight of said potted plant and resisting separation of said second support element from said first support element, a mask element connected to said second support element and adapted to be moved along said first support element in response to movement of said second support element relative to said first support element, an indicator element with an indication indicia, and mounting means for mounting said indicator element on said first support element and for adapting said indicator element so that it moves in response to relative motion between said first and second support elements, said mask element cooperating with said indicator element in such a manner as to cover said indication indicia when said potted plant is watered and to expose said indicia as said potted plant dries out, said mounting means comprising means for mounting said indicator element on said first support element so that said indicator element remains in a fixed position on said first support element absent a moving force, slippage means on said indicator element operable whenever the direction of relative motion between said first and second support elements is reversed, for allowing said indicator element to remain fixed in position for a predetermined distance of movement of said mask element sufficient either to cover or expose said indicia before said moving force is applied to said indicator element.

2. The apparatus of claim 1 wherein said slippage means comprises a slot in said indicator element, said slot has a length along the direction of relative motion between said support elements, and said length defines said predetermined distance.

3. The apparatus of claim 2 wherein said mask element is attached to said second support element by a member passing through said slot in said indicator element.

4. The apparatus of claim 3 wherein said indication indicia is a brightly-colored band on one end of said indicator element and said band has a height on the order of said length, whereby said band is covered during watering and exposed after said potted plant has dried out.

5. The apparatus of claim 4 wherein said first support element is a tubular housing with a hook means on one end.

6. The apparatus of claim 5 wherein said second support element is a rod with a hook means on one end.

7. The apparatus of claim 6 wherein said spring means is a helical spring which is contained within said tubular housing and which surrounds said rod.

8. The apparatus of claim 7 wherein said indicator element is a band gripping the exterior of said tubular housing.

9. The apparatus of claim 8 wherein said mask element is connected to said rod by an element extending through a slot running along the length of said housing and through said slot in said indicator element.

10. The apparatus of claim 9 wherein said mask element covers a portion of said indicator element and said indicia is a brightly-colored band of a size such that it is covered by said mask element when said potted plant is watered and said mask element is thereby moved downward relative to said housing by at least said predetermined length, and such that it is uncovered by said mask element when said potted plant dries out and said mask element is thereby moved upward relative to said housing by at least a portion of said predetermined length.

11. The apparatus of claim 10 wherein said spring means comprises a compression spring located within said tubular housing.

* * * * *